United States Patent [19]

Katz et al.

[11] Patent Number: 4,788,379
[45] Date of Patent: * Nov. 29, 1988

[54] PRODUCTION OF ACETYLENE

[75] Inventors: Michael Katz, New City, N.Y.; Frank Carluccio, Towaco, N.J.; Gil Mallari, Jersey City, N.J.; Kevin FitzPatrick, Irvington, N.J.; Ashok Desai, Wayne, N.J.; Robert Casciano, Hewitt, N.J.; Jane Tsai, Upper Montclair, N.J.

[73] Assignee: GAF Corporation, Wayne, N.J.

[*] Notice: The portion of the term of this patent subsequent to Jan. 4, 2000 has been disclaimed.

[21] Appl. No.: 432,214

[22] Filed: Oct. 1, 1982

Related U.S. Application Data

[63] Continuation of Ser. No. 219,756, Dec. 23, 1980, Pat. No. 4,367,363.

[51] Int. Cl.[4] .............................................. C07C 7/10
[52] U.S. Cl. ..................................... 585/809; 585/534; 585/538; 585/539; 585/540; 585/834
[58] Field of Search ............... 585/534, 538, 539, 540, 585/809, 834

[56] References Cited

U.S. PATENT DOCUMENTS

| | | | |
|---|---|---|---|
| 2,964,551 | 12/1960 | Woolcock | 585/809 X |
| 3,234,712 | 2/1966 | Lovett et al. | 585/809 X |
| 3,471,584 | 10/1969 | Platz et al. | 585/809 X |
| 3,657,375 | 4/1972 | Brunner et al. | 585/809 X |
| 3,686,344 | 8/1972 | Brunner et al. | 585/809 X |
| 4,105,888 | 8/1978 | Fey | 585/539 X |
| 4,367,363 | 1/1983 | Katz et al. | 585/809 |

Primary Examiner—Charles F. Warren
Attorney, Agent, or Firm—Marilyn J. Maue; Joshua J. Ward

[57] ABSTRACT

The process relates to the recovering of essentially pure acetylene from the gaseous out-put stream from a coal to acetylene conversion process. A plasma arc generator or other high energy type reactor can be used for the conversion to coal. The gaseous out-put stream is initially treated in an acid gas removal stage by absorbing HCN and $H_2S$ in an organic solvent such as N-methyl pyrrolidone and scrubbing with a caustic agent such as NaOH to remove $CO_2$. In a second stage, the gaseous out-put stream is scrubbed with the organic solvent to provide a sweet gas treatment and remove essentially pure acetylene as a product. In a third stage, the second stage gases are first hydrogenated, then desulfurized and then methanated. The out-put from the third stage is recycled to the coal to acetylene conversion process. In a fourth stage, the organic solvent from said second stage is refined and recycled to the first stage and/or second stage.

7 Claims, 6 Drawing Sheets

PRODUCTION OF ACETYLENE

This is a continuation of application Ser. No. 219,756 filed Dec. 23, 1980 and now U.S. Pat. No. 4,367,363.

BACKGROUND OF THE INVENTION

1. Field of the Invention

This invention relates to the production of acetylene from a feed stream which contains impurities such as HCN, $H_2S$, $CS_2$, CO and $CO_2$.

2. Brief Description of the Prior Art

The acetylene rich output from reactors such as plasma art reactors, radiant energy reactors and the like, have great value if the acetylene can be separated as a high yield product, free of impurities and if the process can be run under reasonable economic conditions.

The removal of acidic gases from gaseous mixtures is disclosed in U.S. Pat. No. 3,565,573, the removal of $CO_2$ and the washing of acetylene with an organic solvent is disclosed in U.S. Pat. No. 3,686,344, acetylene separation is disclosed in U.S. Pat. No. 3,325,972, the removal of hydrogen cyanide from acidic gases is disclosed in U.S. Pat. No. 3,935,188 and the removal of $H_2S$ and $CO_2$ is disclosed in U.S. Pat. No. 3,829,521, as examples of available technology. However, an integrated system is required to achieve the desired end result within the frame work of the economic restraints of a commercial system.

SUMMARY OF THE INVENTION

In accordance with the present invention, pure acetylene is produced from a feed stock which includes such impurities as $H_2S$, $SC_2$, CO and $CO_2$. In a first stage acid gases such as HCN and $H_2S$ are selectively removed using an amine or an alkyl pyrrolidone solvent and $CO_2$ is removed using a caustic scrubber. In a second stage, the same solvent is preferably used to remove $CS_2$ and produce an acetylene rich product. In a third stage, the remaining gases are subjected to hydrogenation and desulferization prior to methanation and then recycled to a coal to acetylene reactor.

BRIEF DESCRIPTION OF THE DRAWINGS

The objects and advantages of the invention will become apparent from the following description of the inventory, particularly when read in conjunction with the drawings herein.

DESCRIPTION OF THE PREFERRED EMBODIMENTS

Figure 1:
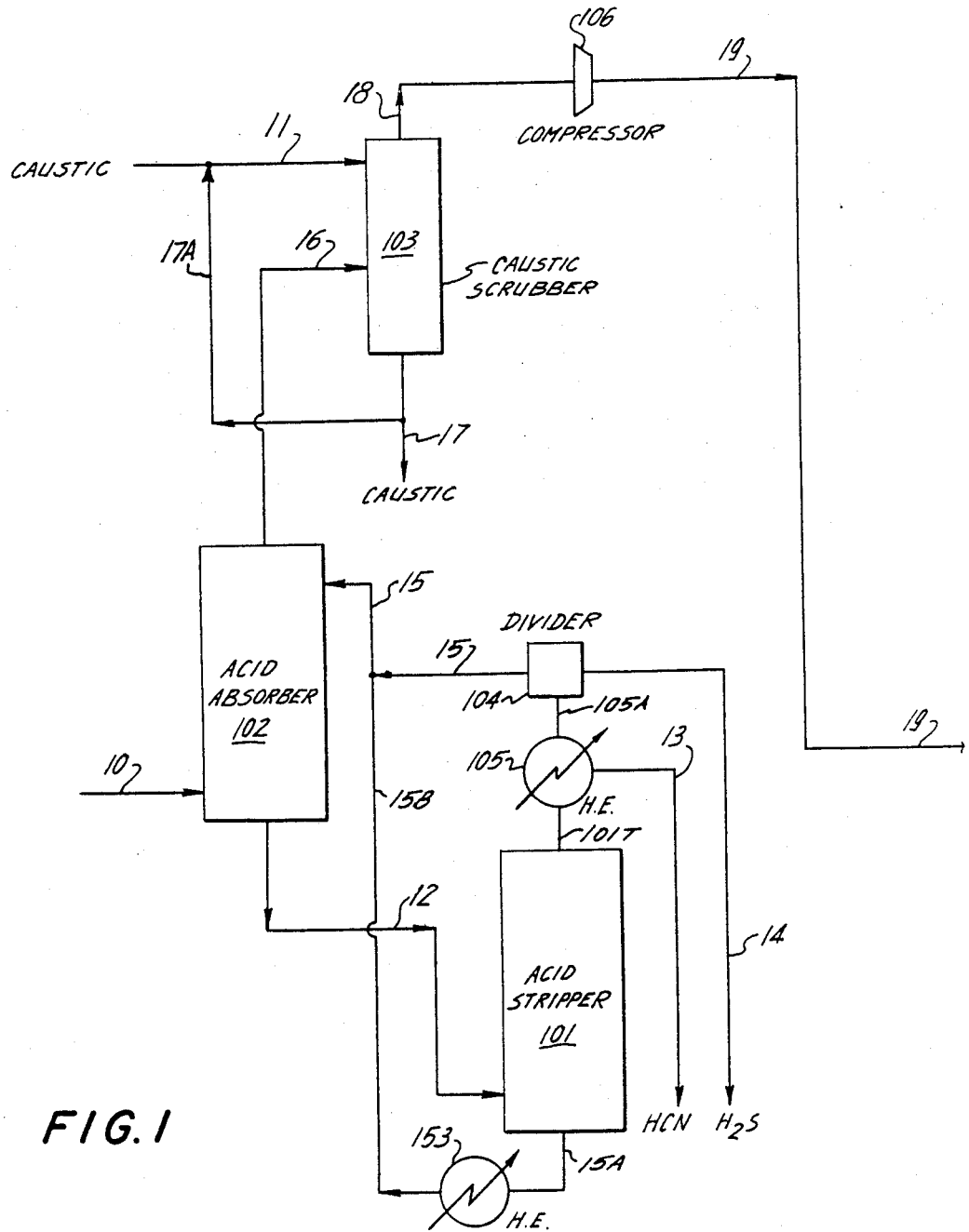
FIG. 1 is a schematic representation of a first part of the acid gas clean-up portion of the process.
Figure 2:
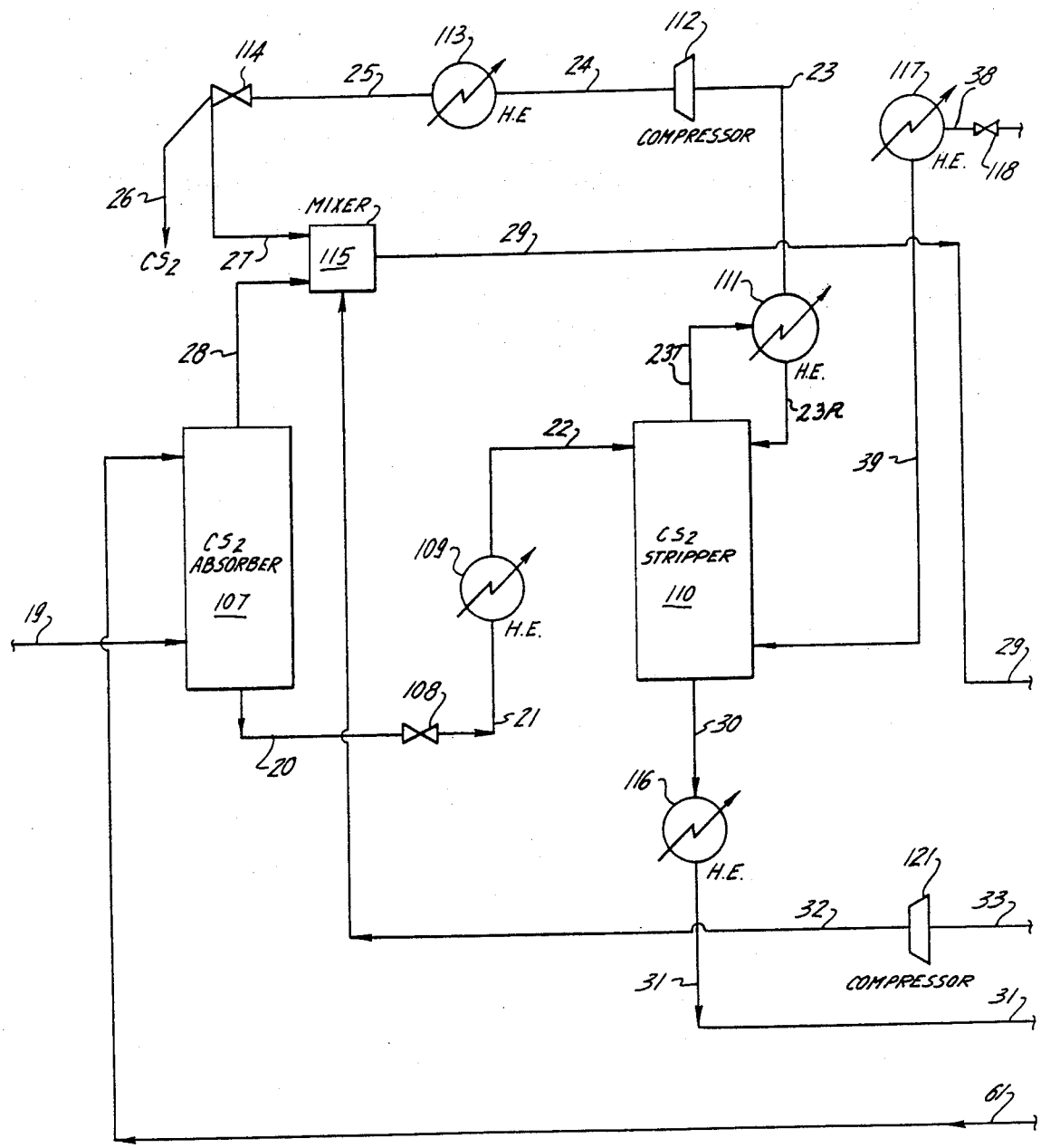
FIG. 2 is a schematic representation of a first part of the sweet gas clean-up portion of the process.
Figure 3:
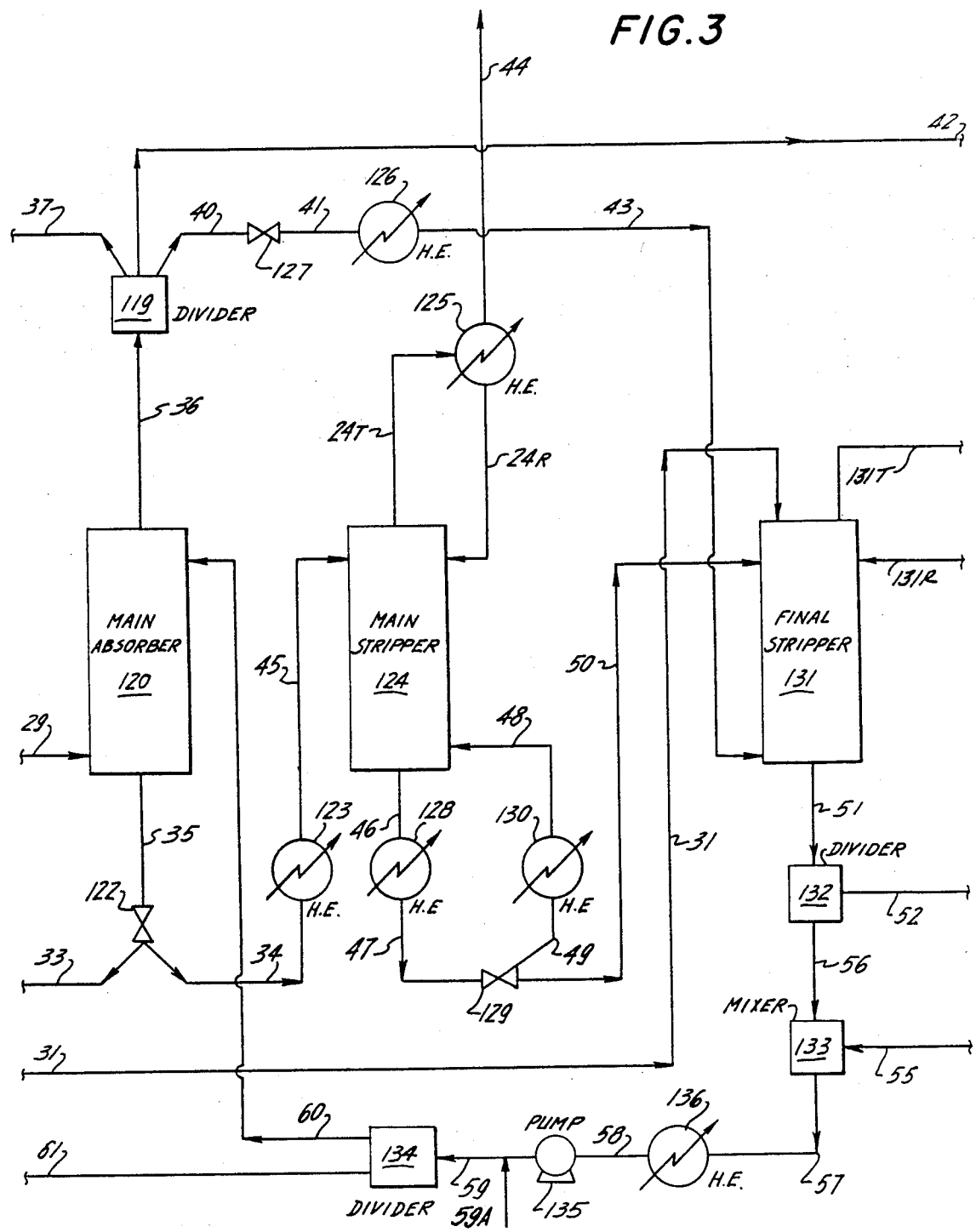
FIG. 3 is a schematic representation of a second part of the sweet gas clean-up operation.
Figure 4:
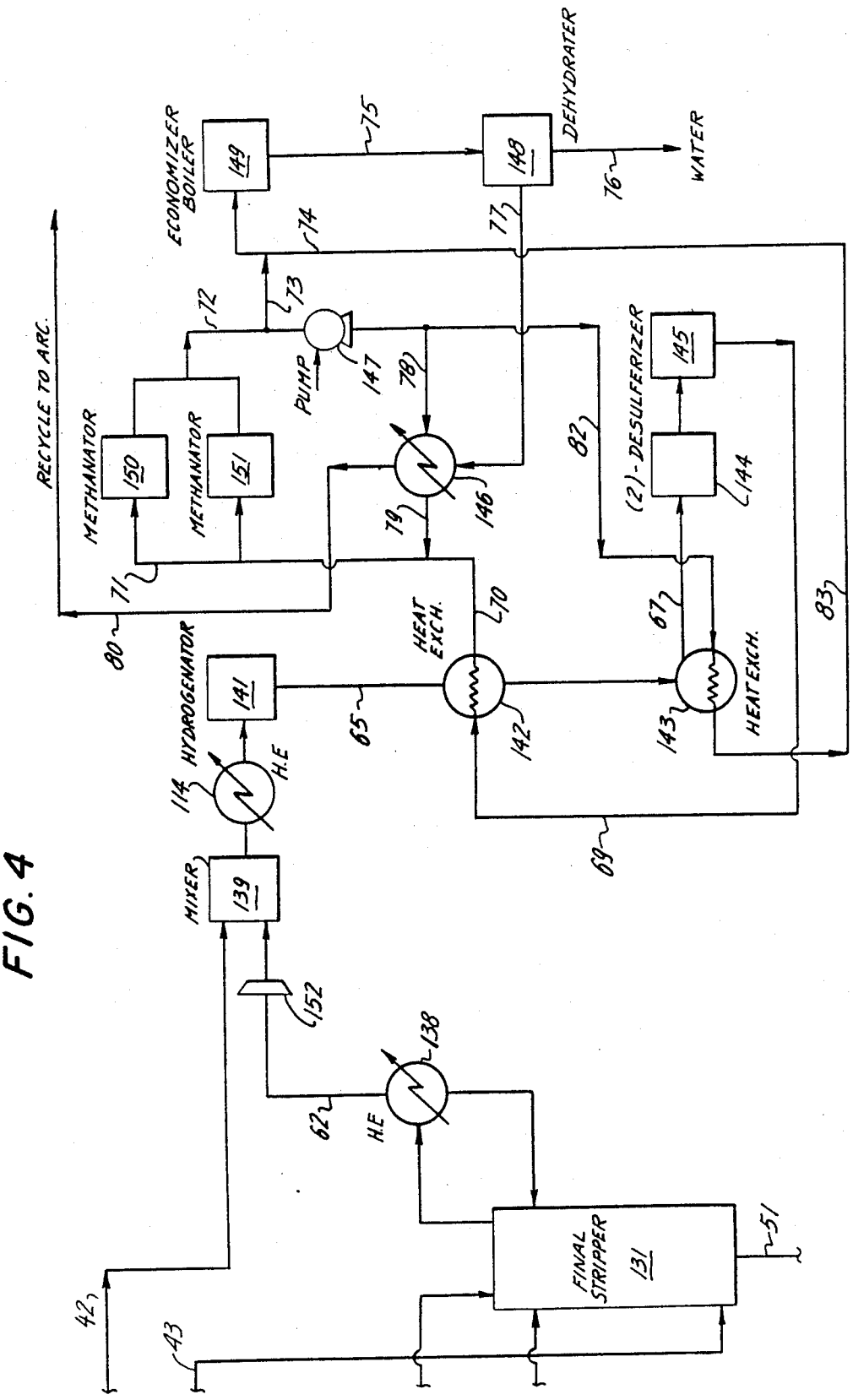
FIG. 4 is a schematic illustration of the hydrogenation, desulfurization and methanation portion of the process.
Figure 5:
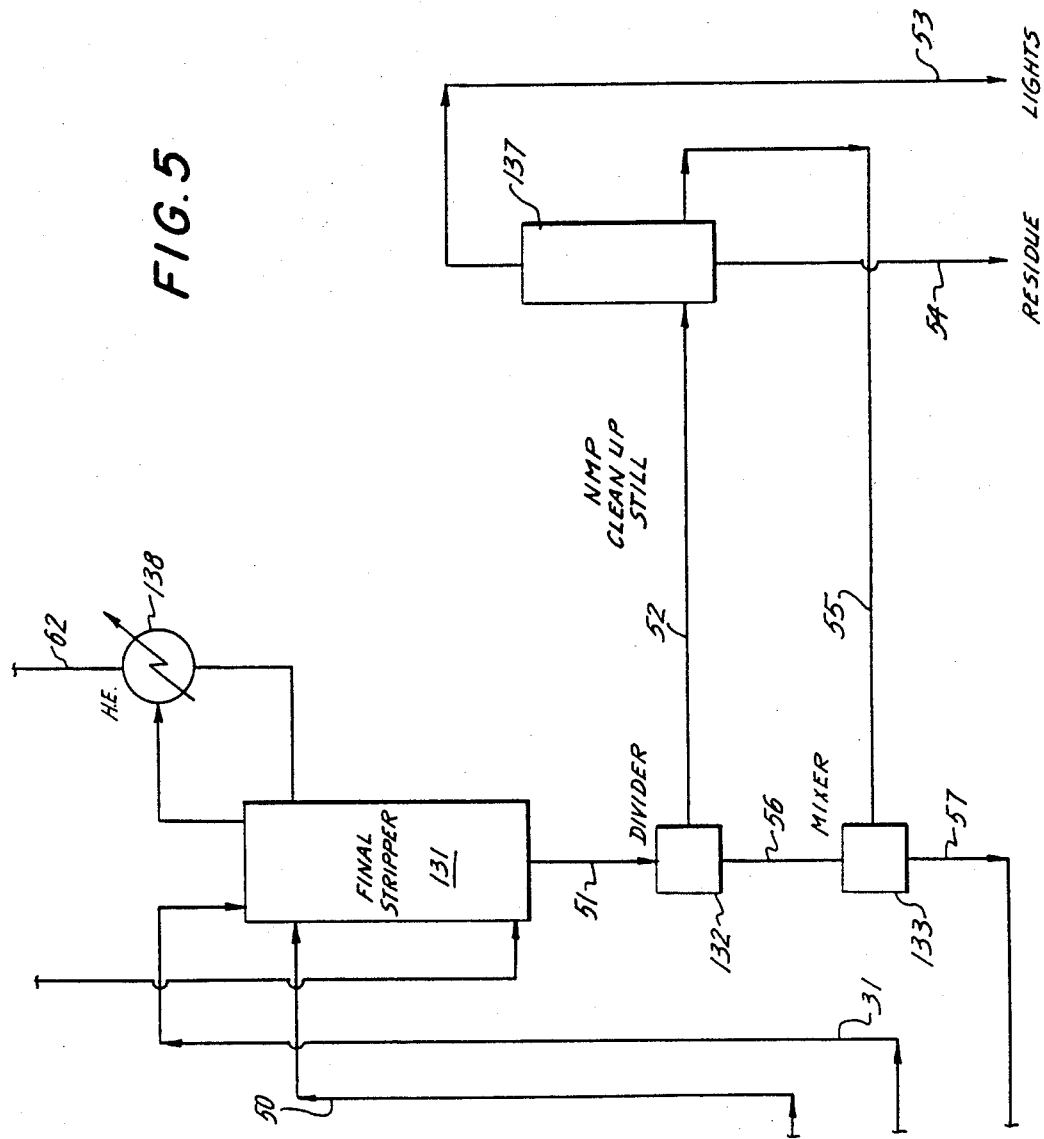
FIG. 5 is a schematic illustration of the organic solvent clean-up portion of the process.
Figure 6:
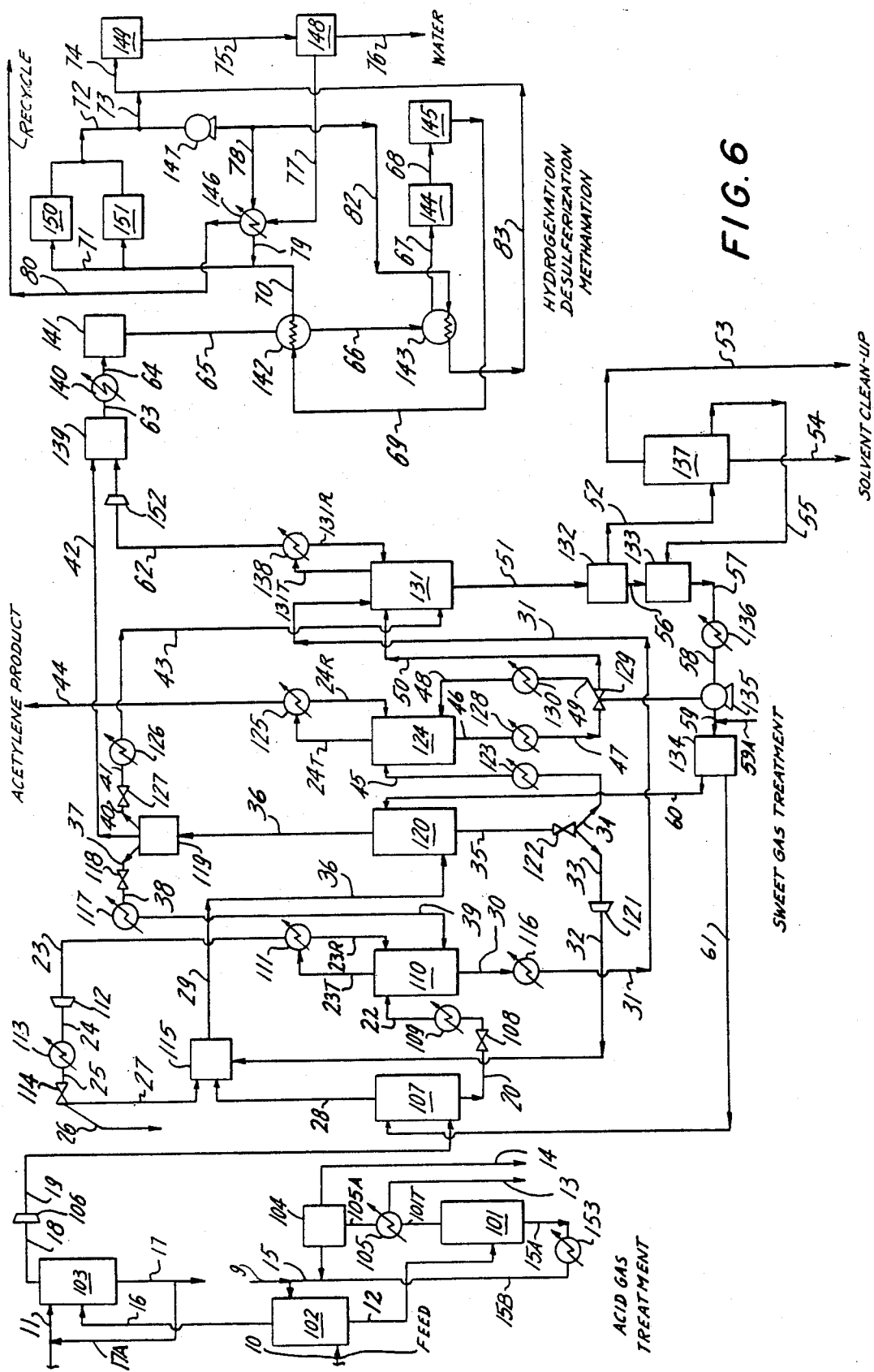
FIG. 6 is a schematic illustration of the overall process.

The acetylene gas separation process includes four stages of operation. The gas first goes through an acid gas removal section where HCN and $H_2S$ are selectively removed utilizing 5% NMP in water as the absorption solvent. The $CO_2$ is then removed with a caustic scrubber. The gas then passes to the second stage.

In the second stage, $CS_2$ is removed using NMP as the solvent, and acetylene is separated from the other gasses ($H_2$, $CH_4$, $C_2H_2$, $C_2H_4$, $C_3H_4$, $C_4H_2$, CO).

In the third stage, the remaining gasses are hydrogenated, desulfurized and methanated. The treated gasses are then recycled to the source. Any hydrogen blowdown would occur at this point.

The fourth stage is the NMP cleanup, where NMP is purified via limestone treat and distillation.

The feed 10 can be the output from an acetylene gas generation system such as an arc generator of the type disclosed in U.S. Pat. Nos. such as 3,333,027, 4,105,888 and 4,010,090 and high temperature reactors of the type disclosed in U.S. Pat. No. 3,933,434 or other acetylene generator systems, such as U.S. Pat. No. 3,384,467. Similarly, other forms of acetylene generators can be used as the source of the feed stream.

The feed stream 10 is treated in an acid absorber 102 with an organic solvent, which is preferably an alkylamine or alkyl pyrrolidone such as N-methyl pyrrolidone.

From absorber 102 the organic solvent and almost all of the HCN and $H_2S$ are removed as bottoms via line 12 and fed to an acid stripper 101. Overhead from stripper 101 is removed via line 101T and cooled in a heat exchanger 105 to condense HCN. Condensed HCN is removed from the system via line 13. The remainder of the cooled overhead from stripper 101 passes through line 105A to a divider 104 in which $H_2S$ and organic solvent are separated. $H_2S$ is removed from the system via line 14 and solvent, along with makeup solvent introduced through line 9, is recycled to absorber 102 via line 15. Bottom from stripper 101 is recycled to absorber 102 via lines 15A and 15B and heat exchanger 153.

Overhead from absorber 102 is rich in the $H_2$, CO, $CH_4$, $C_2H_4$, $C_2H_2$, $C_3H_4$, $C_4H_2$, $CS_2$ and $CO_2$ of the feed stream. This overhead is removed from absorber 102 and passed via line 16 to a caustic scrubber 103 in which it is treated with a caustic such as NaOH to separate residual HCN and most of the residual $H_2S$. Caustic is introduced to the scrubber 103 via line 11. From scrubber 103 bottoms containing HCN, $H_2S$, $CO_2$ and caustic are removed via line 17. A portion of this bottoms material is withdrawn from the system via line 17 and the remainder is recycled to the scrubber via lines 17A and 11. The overhead effluent from the caustic scrubber 103 is removed via line 18, compressed in a compressor 106 and fed via line 19 to a $CS_2$ absorber 107 in which an organic solvent is used which is preferably the same solvent used in acid absorber 102. The $CS_2$ and $C_4H_2$ is essentially removed, along with most of the $C_3H_4$ and some $C_2H_4$, via line 20 and delivered to a $CS_2$ stripper 110 after passing through reduction valve 108 and being cooled in heat exchanger 109. Overhead is removed from absorber 107 via line 28 and passed to a mixer 115.

A bottom stream containing $C_3H_4$ and N-methyl pyrrolidone is removed from the bottom of stripper 110 via line 30 and passed through heat exchanger 116 and line 31 to a final stripper 131.

The overhead stream from stripper 110 is removed via line 23T and cooled in reflux heat exchanger 111 from which a portion is returned to the stripper 110 as reflux via line 23R. The remaining portion passes via line 23, compressor 112 and line 24 to heat exchanger 113 where it is cooled and passed via line 25 to flash tank 114. In flash tank 114 the $CS_2$ along with minor amounts of $C_2H_2$, $C_3H_4$ and $C_4H_2$ are separated and removed from the process via line 26. More volatile constituents including $H_2$, CO, $CH_4$, $C_2H_4$ and $C_2H_2$ are passed via line 27 to mixer 115. From mixer 115 a combined stream which is high in $H_2$, CO, $CH_4$, $C_2H_4$ and $C_2H_2$ is passed via line 29 to a main absorber 120. Main absorber 120 uses an organic solvent, preferably the same solvent as used in other parts of the system, to strip most of the $C_2H_2$ from the combined streams.

Overhead is removed from absorber 120 through line 36 and passed to a divider 119. From divider 119 a first portion of the overhead from absorber 120 is passed via line 42 to the hydrogenation portion of the process. A second portion of the overhead from absorber 120 is recycled to stripper 110 via lines 37 and 38, valve 118, heat exchanger 117 and line 39. A third portion of the overhead from absorber 120 passes from divider 119 to a final stripper 131 via lines 40 and 41, valve 127, heat exchanger 126 and line 43.

A bottoms fraction is removed from absorber 120 via line 35 and flash separated at 122 into a gaseous stream which is passed via line 33 to a compressor 121 and a liquid stream which is passed via line 34 to a heat exchanger 123. From compressor 121 the gaseous stream returns via line 32 to mixer 115. The liquid portion passes from heat exchanger 123 to a main stripper 124 via line 45. From stripper 124 overhead product is removed via line 24T and cooled in reflux heat exchanger 125. Reflux is returned to stripper 124 via line 24R and acetylene product is removed through line 44. A bottoms fraction containing the organic solvent and primarily $C_2H_4$ with some $C_3H_4$, $C_4H_2$ and $CS_2$ is removed from stripper 124 through line 46, heated in heat exchanger 128 and passed through line 47 to flash drum 129. From flash drum 129 a liquid stream containing most of the organic solvent and $C_2H_4$, $C_3H_4$ and minor amounts of $C_4H_2$, $CS_2$ and organic solvent is passed via line 50 to stripper 131. The gaseous stream from flash drum 129 is passed via line 49 to heat exchanger 130 where it is cooled and returned to the bottom of main stripper 124 via line 48.

Overhead is removed from stripper 131 via line 131T and heated in reflux heat exchanger 138 with a portion being returned to stripper 131 via line 131R and the remainder being passed via line 62 to a compressor 152 and thence to mixer 139.

From stripper 131 bottoms are withdrawn via line 51 to divider 132 where they are subjected to limestone treatment. From the divider 132 a portion of the bottoms are passed via line 52 to distillation column 137. From column 137 bottoms which consist essentially of organic solvent and low molecular weight polymer are withdrawn via line 54 and overhead which is a mixture of hydrogen, $C_4H_2$ and organic solvent is withdrawn via line 53. A stream of mostly solvent is removed from column 137 via line 55 and passed to a filtration mechanism 133 in which it is mixed with a portion of bottoms from stripper 131 which is introduced via line 56 from divider 132. From the filtration mechanism a predominantly organic solvent stream is withdrawn through line 57, heated in heat exchanger 136 and passed via line 58 to pump 135 and then via line 59 to divider 134 along with make up solvent which may be introduced through line 59A. From divider 134 a portion of the solvent is recycled to absorber 107 via line 61 and a portion is recycled to absorber 120 via line 60.

From mixer 139 the overhead portions from stripper 131 and absorber 120 are passed through line 63, heat exchanger 140 and line 64 to a catalytic hydrogenator 141 in which a portion of the hydrogen, $C_2H_4$, $C_3H_4$ and $C_4H_2$ is converted into $C_2H_6$, $C_3H_6$ and $C_4H_{10}$. The hydrogen stream is then passed via lines 65, 66 and 67 and heat exchangers 142 and 143 to a desulfurizer 144 and thence via line 68 to a second desulfurizer 145. From desulfurizer 145 the desulfurized material is passed via line 69, heat exchanger 142, line 70 and line 71 to parallel methanators 150 and 151.

One portion of the product from the methanators 150 and 151 passes through line 72, pump 147, line 78, heat exchanger 146 and line 79 for recycle to the methanators via line 70. A second portion of the methanator product passes through line 73 and 74 to economizer boiler 149. The portion of the methanator product passing through pump 147 which is not recycled to the methanators via lines 78, 79 and 70 is passed via line 82 through heat exchanger 143 and then to economizer boiler 149 via line 83.

From economizer boiler 149 product from the methanators passes through line 75 to a second economizer boiler 148 from which water is removed via line 76. The methanator product then passes from boiler 148 through line 77 and heat exchanger 146 from which it may be recycled via line 80 to the coal to acetylene conversion process which may be the source of the feed introduced to the process through line 10.

EXAMPLE

The following example sets forth the process parameters and the material and energy balances for the separations of a plurality of end products and impurities from the output of a plasma arc reactor of the type disclosed in U.S. patents.

The Tables I through VIII set forth the compositions of each stream in Lb. Mole per hour, unless othewise specified, temperatures, pressures, and in some instances, enthalpy and liquid or vapor flow rates.

The reflux heat exchanges 111, 125, 105 and 138 specifications are set forth in Table IX.

The scrubber, absorber and stripper column specifications are set forth in Table X.

The N-methyl pyrrolidone distillation tower 137, is a 10 tray tower operating at 4000 MM Hg., at 360° F. and handles 100 lb. moles per hour of feed.

The hydrogenator, desulferizers and methanators employ catalysts which are commonly used for the respective function. It should be noted that the process design calls for conventional equipment as well known in the art.

TABLES

The foregoing described process is noted to depart from the state of the art in a variety of ways. For example, the system generates acetylene from gassified coal with acid gas levels in the 1 to 5% range and acetylene in the 3 to 20% range and the sweet gas system uses pressure vessels only, and thus avoids the expense associated with vacuum systems, $H_2S$, $CS_2$, HCN and $C_2H_2$ are recovered as pure, unreacted products. Furthermore, the unique equipment train and process sequence uses an alkyl amine or an alkyl pyrrolidone in dilute form to remove $H_2S$ and HCN as well as in the sweet gas section and thus is a one solvent system.

As a further feature, overhead gases are used to reduce concentration gradients in the stripping operations and thus enhance stripping. The use of conditioning equipment in the recycle stream boosts the yield by enabling the recycling of hydrocarbon stream. The desulferization prior to methanation avoids the poisoning of the methanator catalyst.

TABLE I

ACID GAS LB. MOLES/HR.

| Stream | 10 | 12 | 14 | 13 | 15 | 16 | 18 | 17 | 65 |
|---|---|---|---|---|---|---|---|---|---|
| $H_2$ | 12,225 | 4.28 | 4.28 | 0 | 0 | 12,221 | 12,221 | 0 | 0 |
| CO | 620 | 1.43 | .57 | 0 | .15 | 620 | 620 | .29 | 25.7 |
| $CH_4$ | 171 | .29 | .29 | 0 | 0 | 171 | 171 | 0 | 0 |
| $C_2H_4$ | 128.3 | 0 | 0 | 0 | 0 | 128.3 | 128.3 | 0 | 0 |
| $C_2H_2$ | 1,677 | 17.1 | 17.1 | 0 | 0 | 1,660 | 1,660 | 0.6 | 51.3 |
| $C_3H_4$ | 11.4 | 0 | 0 | 0 | 0 | 11.4 | 11.4 | 0 | 0 |
| $C_4H_2$ | 11.4 | 0 | 0 | 0 | 0 | 11.4 | 11.4 | 0 | 0 |
| $CS_2$ | 28.5 | 0.15 | 0.15 | 0 | 0 | 28.5 | 28.5 | 0.15 | 12.8 |
| 5% NMP in $H_2O$ | 0 | 9,975 | 0 | 0 | 9,975 | 0 | 0 | 0 | 0 |
| 10% NaOH in $H_2O$ | 0 | 0 | 0 | 0 | 0 | 0 | 0 | 114 | 10,260 |
| $CO_2$ | 12.8 | 0.29 | 0.29 | 0 | 0 | 12.8 | 1.43 | 11.4 | 1,026 |
| $H_2S$ | 28.5 | 27.1 | 27.1 | 0 | 0 | 1.43 | 0.29 | 1.43 | 128.3 |
| HCN | 178 | 178 | 0.29 | 178 | 0.29 | 0.6 | 0 | 0.6 | 51.3 |
| Temp., °F. | 77 | 77 | 95 | 120 | 90 | 77 | 77 | 89 | 77 |
| P., psia | 29 | 29 | 14.7 | 14.7 | 29 | 29 | 29 | 14.7 | 14.7 |

TABLE II

SWEET GAS LB. MOLES/HR.

| Stream | 19 | 20 | 21 | 22 | 28 | 27 | 26 | 25 | 24 | 23 |
|---|---|---|---|---|---|---|---|---|---|---|
| $H_2$ | 12,220 | 5.9 | 5.9 | 5.9 | 12,215 | 255 | 0.40 | 255 | 255 | 255 |
| CO | 619 | 0.34 | 0.34 | 0.34 | 618 | 12.9 | 0.02 | 12.9 | 12.9 | 12.9 |
| $CH_4$ | 171 | 0.23 | 0.23 | 0.23 | 171 | 3.8 | 0 | 3.8 | 3.8 | 3.8 |
| $C_2H_4$ | 129 | 1.0 | 1.0 | 1.0 | 128 | 3.4 | 0.07 | 3.5 | 3.5 | 3.5 |
| $C_2H_2$ | 1,660 | 233 | 233 | 233 | 1,427 | 181 | 51.5 | 233 | 233 | 233 |
| $C_3H_4$ | 10.9 | 7.6 | 7.6 | 7.6 | 3.3 | 3.1 | 4.6 | 7.6 | 7.6 | 7.6 |
| $C_4H_2$ | 11.4 | 12.0 | 12.0 | 12.0 | 0.1 | 0.2 | 4.8 | 5.0 | 5.0 | 5.0 |
| $CS_2$ | 28.2 | 28.2 | 28.2 | 28.2 | 0.1 | 1.5 | 25.7 | 27.3 | 27.3 | 27.3 |
| NMP | | 1138. | 1138. | 1138. | 0.7 | | 0.7 | 0.7 | 0.7 | 0.7 |
| Temp., °F. | 77 | 79.9 | 72.3 | 266 | 86.5 | 10 | 10 | 10 | 677 | 100 |
| P., psia | 225 | 225 | 14.7 | 14.7 | 225 | 225 | 225 | 225 | 225 | 14.7 |
| Enthalpy, BTU/Hr. | $.49 \times 10^7$ | $-.26 \times 10^8$ | $-.26 \times 10^8$ | $-.15 \times 10^8$ | $.58 \times 10^7$ | $-.13 \times 10^6$ | $-.73 \times 10^6$ | $-.87 \times 10^6$ | $.35 \times 10^7$ | $.33 \times 10^6$ |
| Vol. Flow Rate (gpm) liquid | | 250 | 236 | 237 | | | | 9.4 | 9.4 | |
| Vol. Flow Rate (ft.$^3$/sec.) vapor | 106 | | 13.6 | 41.3 | 106 | 2.80 | | 2.80 | 8.28 | 62.1 |

TABLE III

SWEET GAS LB. MOLES/HR.

| Stream | 30 | 31 | 39 | 38 | 37 | 42 | 40 | 41 | 43 | 29 |
|---|---|---|---|---|---|---|---|---|---|---|
| $H_2$ | 0.3 | 0.3 | 250 | 250 | 250 | 11,357 | 874 | 874 | 874 | 12,549 |
| CO | 0.01 | .01 | 12.7 | 12.7 | 12.7 | 575 | 44.2 | 44.2 | 44.2 | 635 |
| $CH_4$ | 0.01 | .01 | 3.5 | 3.5 | 3.5 | 159. | 12.2 | 12.2 | 12.2 | 180. |
| $C_2H_4$ | 0.02 | .02 | 2.5 | 2.5 | 2.5 | 116. | 8.9 | 8.9 | 8.9 | 143. |
| $C_2H_2$ | 0 | 0 | .03 | .03 | .03 | 1.7 | .1 | .1 | .1 | 2,249 |
| $C_3H_4$ | 0 | 0 | 0 | 0 | 0 | 0 | 0 | 0 | 0 | 6.8 |
| $C_4H_2$ | 7.0 | 7.0 | 0 | 0 | 0 | .1 | 0 | 0 | 0 | .34 |
| $CS_2$ | .8 | .8 | 0 | 0 | 0 | .02 | 0 | 0 | 0 | 1.7 |
| NMP | 1137 | 1137 | .0 | 0 | 0 | .50 | 0 | 0 | 0 | 1.25 |
| Temp., °F. | 242.6 | 350 | 266 | 77.8 | 77.2 | 77.2 | 77.2 | 77.9 | 350 | 112.4 |
| P., psia | 14.7 | 14.7 | 14.7 | 14.7 | 225 | 225 | 225 | 14.7 | 14.7 | 225 |
| Enthalpy, BTU/Hr. | $-.17 \times 10^5$ | $-1.09 \times 10^7$ | $.44 \times 10^6$ | $.86 \times 10^5$ | $.86 \times 10^5$ | $.39 \times 10^7$ | $.30 \times 10^6$ | $.30 \times 10^6$ | $.21 \times 10^7$ | $.93 \times 10^7$ |
| Vol. Flow Rate (gpm) liquid | 237 | 250 | | | | | | | | |
| Vol. Flow Rate (ft.$^3$/sec.) vapor | | .05 | 39.4 | 29.3 | 1.93 | 87.6 | 6.7 | 102 | 154 | 118 |

TABLE IV

SWEET GAS LB. MOLES/HR.

| Stream | 36 | 44 | 35 | 46 | 48 | 32 | 33 | 34 | 45 | 47 |
|---|---|---|---|---|---|---|---|---|---|---|
| $H_2$ | 12,471. | .63 | 79.6 | 0 | 0 | 79.0 | 79.0 | .57 | .55 | 0 |
| CO | 632 | .03 | 4.0 | 0 | 0 | 4.0 | 4.0 | 0 | 0 | 0 |
| $CH_4$ | 174 | .09 | 3.8 | 0 | 0 | 3.6 | 3.6 | .11 | .11 | 0 |
| $C_2H_4$ | 2.1 | 154 | 2,247 | 191.0 | 126 | 641. | 641. | 1,606 | 1,606 | 191 |
| $C_2H_2$ | 129. | 1.60 | 14.4 | 0 | 0 | 12.8 | 12.8 | 1.6 | 1.6 | 0 |
| $C_3H_4$ | .0 | 5.1 | 6.8 | 5.1 | 4.0 | .57 | .57 | 6.3 | 6.3 | 5.1 |
| $C_4H_2$ | .1 | 1.17 | 12.0 | 11.7 | 1.0 | .11 | .11 | 11.9 | 11.9 | 11.7 |
| $CS_2$ | .03 | 0.88 | 25.1 | 1.7 | .2 | .11 | .11 | 2.4 | 2.4 | 1.7 |
| NMP | .57 | 1.86 | 16,940 | 17,074 | 137. | .68 | .68 | 16,939. | 16,939 | 17,074 |
| Temp., °F. | 77.3 | 100 | 90 | 336.3 | 300 | 572.7 | 87.8 | 87.8 | 300 | 350 |
| P., psia | 225 | 14.7 | 225 | 14.7 | 14.7 | 225 | 14.7 | 14.7 | 14.7 | 14.7 |
| Enthalpy, BTU/Hr. | $.42 \times 10^7$ | $1.05 \times 10^6$ | $-.38 \times 10^9$ | $-.21 \times 10^9$ | $.51 \times 10^6$ | $-.49 \times 10^7$ | $-.43 \times 10^7$ | $-.38 \times 10^9$ | $-.19 \times 10^9$ | $-.16 \times 10^9$ |
| Vol. Flow Rate (gpm) liquid | | | 3502 | 3659 | 21.6 | | | 3431 | 3557 | 3720 |
| Vol. Flow Rate (ft.$^3$/sec.) vapor | 84.4 | 159 | | | 25.4 | 10.8 | 82.0 | | 256 | 43.4 |

TABLE V

SWEET GAS LB. MOLES/HR.

| Stream | 49 | 50 | 62 | 51 | 52 | 56 | 55 | 60 | 57 | 61 |
|---|---|---|---|---|---|---|---|---|---|---|
| $H_2$ | 0 | 0 | 870 | .39 | .02 | .39 | 0 | 3.7 | .39 | .2 |
| CO | 0 | 0 | 44.6 | .2 | 0 | .2 | 0 | .23 | .2 | .01 |
| $CH_4$ | 0 | 0 | 12.2 | .1 | 0 | .1 | 0 | .11 | .1 | 0 |
| $C_2H_4$ | 0 | 0 | 8.7 | .2 | 0 | .2 | 0 | .23 | .2 | .01 |
| $C_2H_2$ | 126 | 65 | 64.2 | .01 | 0 | .01 | 0 | .01 | .01 | 0 |
| $C_3H_4$ | 4.0 | 3.0 | 3.0 | 0 | 0 | 0 | 0 | 0 | 0 | 0 |
| $C_4H_2$ | 1.0 | 9.6 | 4.0 | 12.5 | .08 | 12.4 | 0 | 11.6 | 12.4 | .79 |
| $CS_2$ | .2 | 1.5 | 1.5 | .8 | 0 | .8 | 0 | .80 | .8 | .06 |
| NMP | 137. | 16,937. | 7.2 | 18,070. | 114 | 17,960. | 114 | 16,937 | 18,070. | 1,139. |
| Temp., °F. | 350 | 350 | 150 | 324.8 | 324.8 | 324.8 | 350 | 77.5 | 325 | 77.5 |
| P., psia | 14.7 | 14.7 | 14.7 | 14.7 | 14.7 | 14.7 | 14.7 | 225 | 14.7 | 225 |
| Enthalpy, BTU/Hr. | $.19 \times 10^7$ | $-.16 \times 10^9$ | $.89 \times 10^6$ | $-.19 \times 10^9$ | $.13 \times 10^7$ | $-.19 \times 10^9$ | $-1.09 \times 10^6$ | $-.38 \times 10^9$ | $-.19 \times 10^9$ | $-.25 \times 10^8$ |
| Vol. Flow Rate (gpm) liquid | | 3722 | | 3722 | 24.6 | 3882 | 25.0 | 3257 | 3907 | 219. |
| Vol. Flow Rate (ft.$^3$/sec.) vapor | 43.6 | | 125 | | | | | | | |

TABLE VI

SWEET GAS LB. MOLES/HR.

| Stream | 59 | 58 | 53 | 54 |
|---|---|---|---|---|
| $H_2$ | .39 | .39 | .02 | 0 |
| CO | .2 | .2 | 0 | 0 |
| $CH_4$ | .1 | .1 | 0 | 0 |
| $C_2H_4$ | .2 | .2 | 0 | 0 |
| $C_2H_2$ | .01 | .01 | 0 | 0 |
| $C_3H_4$ | 0 | 0 | 0 | 0 |
| $C_4H_2$ | 12.4 | 12.4 | .08 | 0 |
| $CS_2$ | .8 | .8 | 0 | 0 |
| NMP | 18,070 | 18,070 | .02 | 2.3 |
| Polymer (NW 200) | 0 | 0 | 0 | 2.3 |
| Temp., °F. | 77.5 | 77 | 90 | 424 |
| P., psia | 225 | 14.7 | 14.7 | 14.7 |
| Enthalpy, BTU/Hr. | $-.41 \times 10^9$ | $-.41 \times 1^9$ | | |
| Vol. Flow Rate, gpm | 3,476 | 3,486 | | |

TABLE VII

SWEET GAS LB. MOLES/HR.

| Stream | 63 | 64 | 65 | 66 | 67 | 68 | 69 | 70 | 79 | 71 | 72 |
|---|---|---|---|---|---|---|---|---|---|---|---|
| $H_2$ | 12,227 | 12,227 | 11,948 | 11,948 | 11,948 | 11,948 | 11,948 | 11,948 | 15,455 | 27,037 | 25,547 |
| CO | 618 | 618 | 618 | 618 | 618 | 618 | 618 | 618 | 0 | 618 | 0 |
| $CH_4$ | 171 | 171 | 171 | 171 | 171 | 171 | 171 | 171 | 1,210 | 1,381 | 2,000 |
| $C_2H_4$ | 125 | 125 | 0 | 0 | 0 | 0 | 0 | 0 | 0 | 0 | 0 |
| $C_2H_2$ | 65.9 | 65.9 | 0 | 0 | 0 | 0 | 0 | 0 | 0 | 0 | 0 |
| $C_3H_4$ | 3.0 | 3.0 | 0 | 0 | 0 | 0 | 0 | 0 | 0 | 0 | 0 |
| $C_4H_2$ | 4.1 | 4.1 | 0 | 0 | 0 | 0 | 0 | 0 | 0 | 0 | 0 |
| $CS_2$ (sulfides) | 1.5 | 1.5 | 1.5 | 1.5 | 1.5 | .6 | .01 | .01 | .01 | .025 | .03 |

TABLE VII-continued

| | SWEET GAS LB. MOLES/HR. | | | | | | | | | | |
|---|---|---|---|---|---|---|---|---|---|---|---|
| | 63 | 64 | 65 | 66 | 67 | 68 | 69 | 70 | 79 | 71 | 72 |
| $H_2O$ | x | x | x | x | x | x | x | x | 947 | 947 | 1570 |
| $C_2H_6$ | x | x | 190 | 190 | 190 | 190 | 190 | 190 | 292 | 482 | 482 |
| $C_4H_{10}$ | x | x | 4.1 | 4.1 | 4.1 | 4.1 | 4.1 | 4.1 | 6.3 | 10.4 | 10.4 |
| $C_3H_6$ | x | x | 3.0 | 3.0 | 3 | 3 | 3 | 3 | 4.6 | 7.5 | 7.5 |
| NMP | 7.7 | 7.7 | 7.7 | 7.7 | 7.7 | 7.7 | 7.7 | 7.7 | 11.7 | 19.5 | 19.5 |
| Temp., °F. | 50 | 400 | 465 | 600 | 650 | 650 | 650 | 515 | 650 | 515 | 800 |
| P., psia | 45 | 44 | 43 | 42 | 41 | 40 | 39 | 38 | 41 | 38 | 37 |

TABLE VIII

| | SWEET GAS LB. MOLES/HR. | | | | | | | |
|---|---|---|---|---|---|---|---|---|
| | 73 | 78 | 82 | 83 | 74 | 75 | 77 | 80 |
| $H_2$ | 8,133 | 15,455 | 1,960 | 1,960 | 10,092 | 10,092 | 8,853 | 8,853 |
| CO | 0 | 0 | 0 | 0 | 0 | 0 | 0 | 0 |
| $CH_4$ | 636 | 1,210 | 153 | 153 | 790 | 790 | 790 | 790 |
| $CS_2$ (sulfides) | .01 | .01 | .01 | .01 | .01 | .01 | .01 | .01 |
| $H_2O$ | 499 | 947 | 120 | 120 | 619 | 619 | 0 | 0 |
| $C_2H_6$ | 153 | 292 | 37 | 37 | 190 | 190 | 190 | 190 |
| $C_4H_{10}$ | 3.3 | 6.3 | .8 | .8 | 4 | 4 | 4 | 4 |
| $C_3H_8$ | 2.4 | 4.6 | .6 | .6 | 3 | 3 | 3 | 3 |
| NMP | 6.2 | 11.7 | 1.5 | 1.5 | 7.6 | 7.6 | 0 | 0 |
| Temp., °F. | 800 | 800 | 800 | 515 | 748 | 100 | 100 | 485 |
| P., psia | 37 | 42 | 42 | 38 | 37 | 32 | 30 | 28 |

TABLE IX

| Number | Q (BTU/hr.) | Reflux Ratio | TC °F. |
|---|---|---|---|
| 111 | 2.4 × 10 | .13 | 100 |
| 125 | 14 × 10 | .32 | 100 |
| 105 | . | .6 | 80 |
| 138 | 22 × 10 | .81 | 150 |

TABLE X

| Number | Name | Dia., ft. | No. Theoretical Trays | Temp. °F. | Pressure, psia |
|---|---|---|---|---|---|
| 107 | $CS_2$ absorber | 5.5 | 10 | 350 | 225 |
| 110 | $CS_2$ stripper | 2.8 | 5 | 300 | 14.7 |
| 120 | Main absorber | 8.7 | 10 | 77 | 225 |
| 124 | Main stripper | 3.1 | 10 | 266 | 14.7 |
| 131 | Final stripper | 10 | 5 | 77 | 14.7 |
| 102 | Acid absorber | | 10 | 77 | 29 |
| 101 | Acid stripper | | 10 | 170 | 14.7 |
| 103 | Caustic scrubber | | 5 | 80 | 29 |

What we claim is:

1. The process for recovering essentially pure acetylene from the gaseous out-put stream from a coal to acetylene conversion process, comprising the steps of:
   (a) processing said gaseous out-put stream in an acid gas removal first stage by absorbing HCN and $H_2S$ in an organic solvent, and scrubbing with a caustic agent to remove $CO_2$;
   (b) scrubbing said gaseous out-put stream with organic solvent in a sweet gas treatment second stage and removing essentially pure acetylene as a product; and
   (c) in a third stage, first hydrogenating, then desulfurizing and then methanating the remaining gases from said second stage.

2. The process of claim 1 wherein said organic solvent is an alkyl amine.

3. The process of claim 1 wherein said organic solvent is an alkyl pyrrolidone.

4. The process of claim 3, wherein said alkyl pyrrolidone is N-methyl pyrrolidone.

5. Process for removal of CO from a gaseous stream containing CO, $H_2$ and unsaturated hydrocarbons which comprises:
   (a) subjecting said stream to hydrogenation conditions to thereby convert the unsaturated hydrocarbons to saturated hydrocarbons;
   (b) then subjecting said stream to methanation conditions to thereby convert CO to $CH_4$ and water; and
   (c) then removing water from said stream.

6. Process according to claim 5 wherein the unsaturated hydrocarbons comprise $C_2H_4$ and $C_2H_2$.

7. Process according to claim 5 wherein the stream also contains $CS_2$ and the stream is subjected to desulfurization conditions after step a and before step b to thereby remove $CS_2$.

* * * * *